(12) United States Patent
Earle

(10) Patent No.: US 8,414,513 B1
(45) Date of Patent: Apr. 9, 2013

(54) TRACTION CONTROL APPARATUS AND METHOD

(76) Inventor: Michael L. Earle, Temple City, CA (US)

( * ) Notice: Subject to any disclaimer, the term of this patent is extended or adjusted under 35 U.S.C. 154(b) by 8 days.

(21) Appl. No.: 13/134,349

(22) Filed: Jun. 7, 2011

(51) Int. Cl.
*A61F 5/00* (2006.01)

(52) U.S. Cl.
USPC ............ 602/32; 602/33; 602/35; 602/36

(58) Field of Classification Search .......... 602/32–39
See application file for complete search history.

(56) References Cited

U.S. PATENT DOCUMENTS

| 2,808,051 | A | * | 10/1957 | Martin | 602/33 |
| 3,149,630 | A | * | 9/1964 | Schmidt | 602/36 |
| 3,385,292 | A | * | 5/1968 | Hardy | 602/36 |
| 3,835,847 | A | * | 9/1974 | Smith | 602/36 |

* cited by examiner

*Primary Examiner* — Michael A. Brown
(74) *Attorney, Agent, or Firm* — William W. Haefliger

(57) ABSTRACT

Patient body part traction exerting and control kit apparatus, comprising in combination a motor driven rotary drive means to tension a traction exerting line; a support means carrying rotary drive means and configured to be attached to equipment at an attraction exertion site, to present drive means for traction line operation attached to aid rotary drive means; the support means having a first section attached to the equipment, and a second section carrying rotary drive means for displacement enabling sideward shifting of a traction line to accommodate patient body shifting, while under traction.

22 Claims, 6 Drawing Sheets

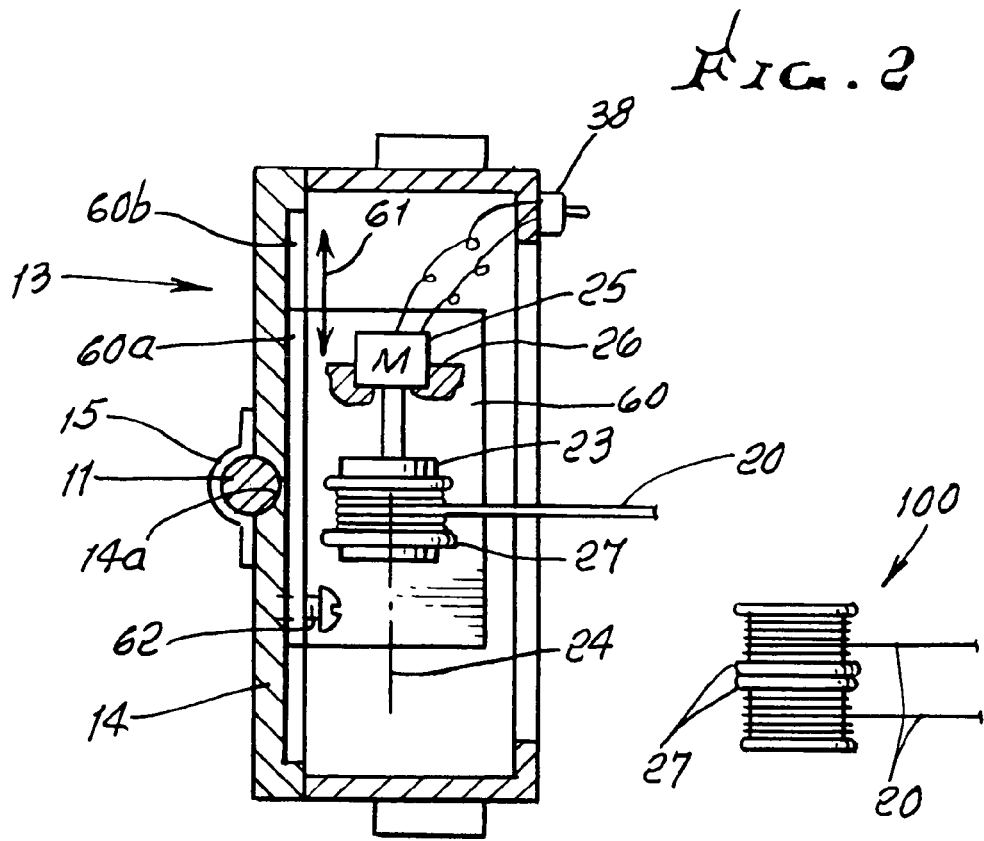
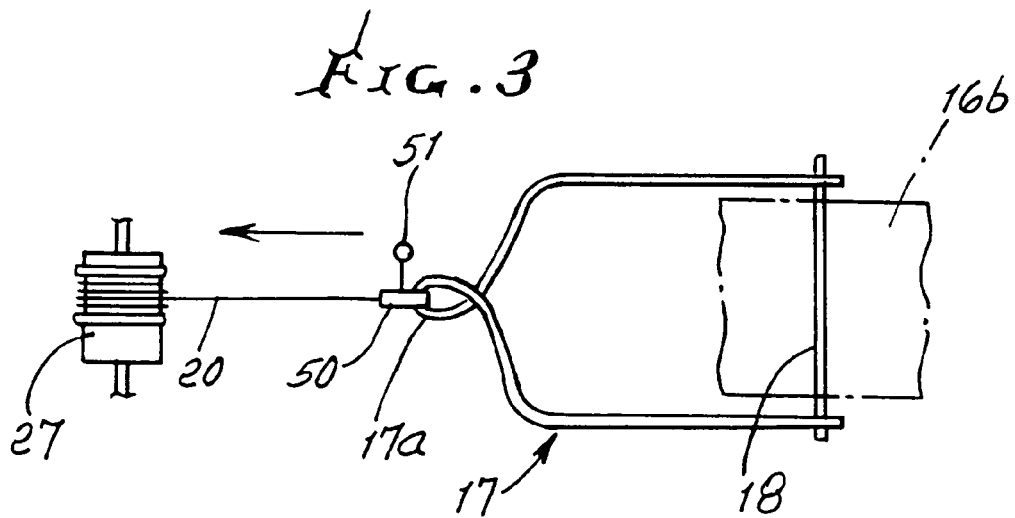

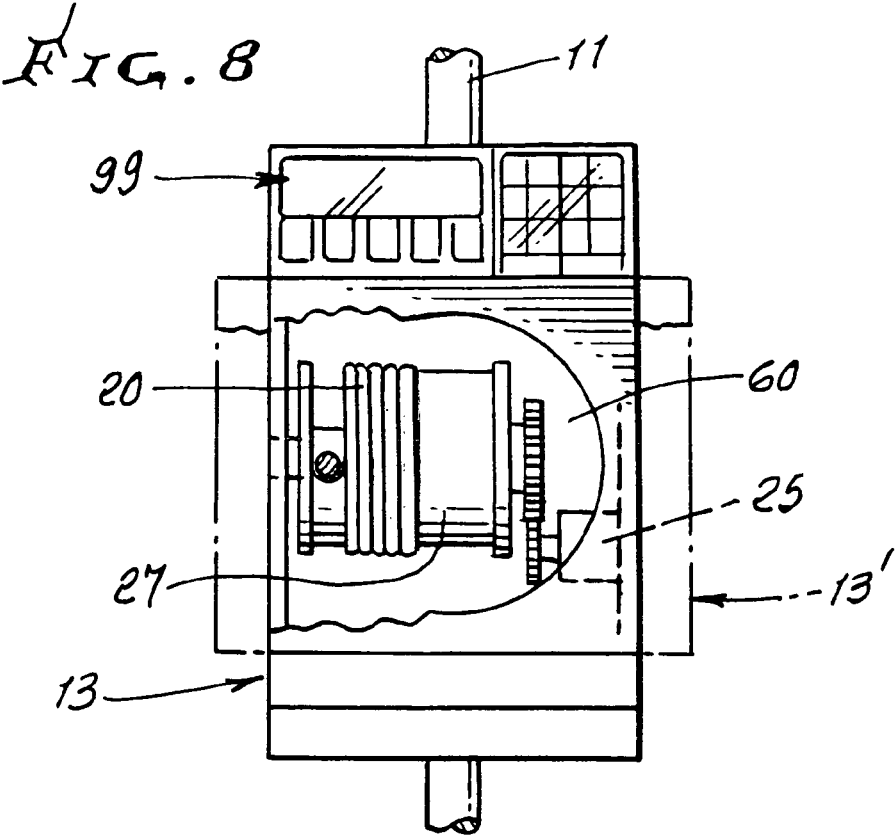
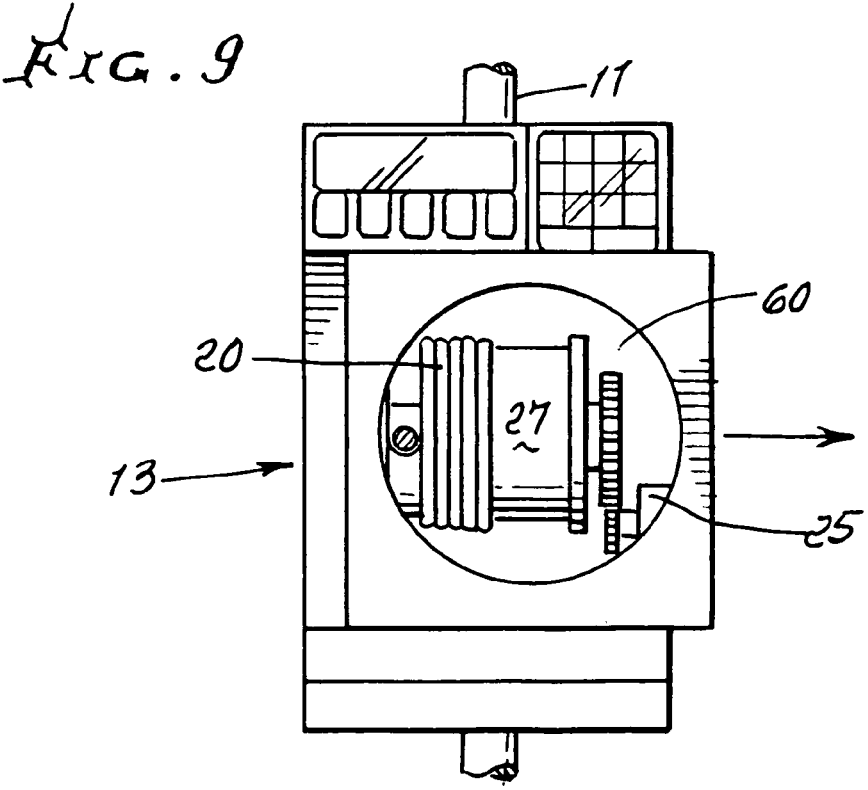

TRACTION CONTROL APPARATUS AND METHOD

BACKGROUND OF THE INVENTION

This invention relates generally to improvements in traction exerting equipment, as applicable to injured patients, and more particularly to precisely adjustable traction exerting equipment useful for fracture management.

Current bedside fracture management requires constant attention and maintenance of cumbersome and sometimes dangerous traction weights. Bedside fracture management technology has remained the same for decades, posing the same problems and patient care issues ongoing. Precise balance, alignment and adequate space are required to fulfill and maintain the delicate physician ordered parameters. Each fracture situation is unique, demanding a high level of attention and care. Natural in-bed patient movement, bedside nursing care, and patient transfer from one point to another are all restricted and encumbered by the use of weighted traction sandbags. As with the evolution of all technology, fracture management technology requires elevation to a new level of performance optimization.

SUMMARY OF THE INVENTION

It is a major object of the invention to provide improved traction management apparatus meeting the above needs. Basically, the equipment is embodied in patient's body part traction exerting and control apparatus comprising in combination:

a) a motor driven rotary drive means to tension a traction exerting line, b) a support means carrying said rotary drive means and configured to be attached to equipment at a traction exertion site, to present said drive means for traction line operation attached to said rotary drive means, c) the support means having a first section attached to said equipment, and a second section carrying the rotary drive means for displacement enabling sideward shifting of the traction line to accommodate patient body shifting, while under traction.

As will be seen, the support means typically has connections enabling selective attachment to said equipment.

Another object includes provision of the support means to comprise a housing containing the rotary drive means in a position to receive attachment of a disposable drum to wind said line. In this regard, the disposable drum presented toward an open side of the housing that passes the line at the time of traction line connection to the patient's body part, for traction exertion.

Another object is to provide controllable electric motor carried by the housing and operatively connected to said rotary drive means for controlling rotation thereof, there being motor controls carried by the housing.

A further object is to provide a supply of the disposable drums, for successive assembly to said rotary drive means at times of traction exertion application to body parts of successive patients.

Yet another object is to provide the second section to have linear displacement connection to said first section. In this regard, the rotary drum means is presented for longitudinal traction line connection, allowing transverse displacement of the rotary drive means.

A yet further object is to provide at least one auxiliary motorized control associated with the apparatus for controlling an auxiliary line that extends to a frame positioned to support said body part under traction. As will be seen, the auxiliary control may be removably carried by said support means or housing. At least two motorized auxiliary controls may be provided for respectively controlling the two auxiliary lines that extend to the frame positioned to support said body part under traction. The two such lines typically extend to two different portions of said frame, to control elevation and tilting thereof.

These and other objects and advantages of the invention, as well as the details of an illustrative embodiment, will be more fully understood from the following specification and drawings, in which:

DRAWING DESCRIPTION

FIG. 2 is a plan view taken in section, diagrammatically showing a kit carrying components of the invention;

FIG. 3 shows a traction means attached to a patient's leg and to a traction force exerting line;

FIGS. 5-9 show alternate forms of the apparatus; and

DETAILED DESCRIPTION

Figure 1:
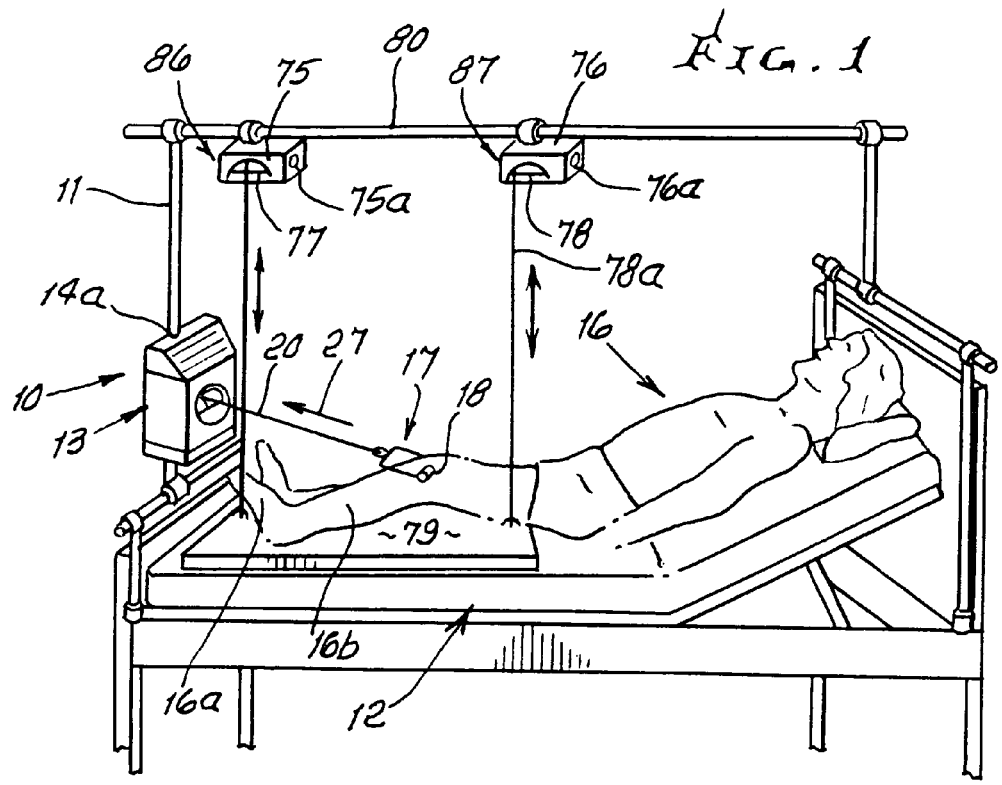
FIG. 1 is a perspective view of a system incorporation the invention.

One preferred form of the patient body part traction exerting and control apparatus is shown in FIGS. 1 and 2. Typically a kit 10 is configured to be attached to a fixed bar 11 at the foot end of a hospital bed 12. A carrier box container 13 forming part of the kit has a rear wall 14 recessed at 14*a* to receive the bar, and a clamp 15, or other means to adjustably hold the kit to the bar, enables vertical adjustment of the kit in relation to the foot 16*a* and leg 16*b* of a patient 16 in bed 12.

FIGS. 1-3 shown a leg traction fork 17 attached at 18 to the leg 16*b*, and having a narrowed looped end 17*a* attached to a traction force exerting line or strand 20. Tension is exerted in arrow indicating direction 21.

A motor driven rotary drive means is provided, as for example a holder such as drum 23 rotated about axis 24, by electric motor 25, located in carrier container. Support means 26 locates the motor in the box, so that axis 24 typically extends generally horizontally. A line winding spool 27 is releasably attached to drum or holder 23. The spool 27 is typically disposable, as is line 20, after use. It is configured to fit on the holder 23 to be released and disposed of after traction exertion is terminated. And a supply 100 of such disposable spools, as with traction lines 20 attached, is shown.

Figure 4:
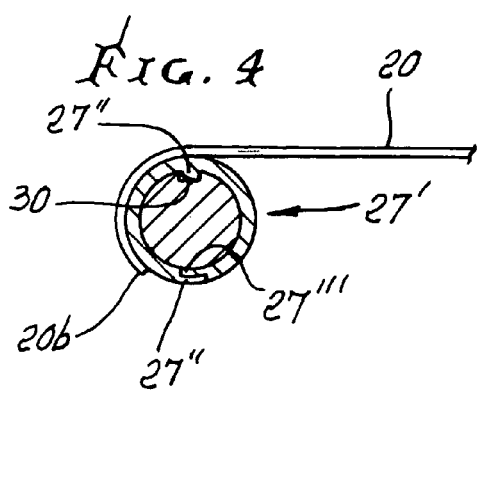
FIG. 4 shows a winding spool attached to a rotary holder or drum.

As an example, note FIG. 4, showing the clam-shell spool 27' having interconnectible end portions at 27", and a tongue 27''' that fits in a groove 30 in the drum 20', to transmit torque from the drum to the spool. Other configurations may be provided enabling spool releasable attachment to the driving drum. Line 20 may be provided already attached, to the spool, as at 20*b* in FIG. 4, enabling spool sidewise or endwise fitting on the drive drum. The open side of the kit box (see opening 35 in front wall 34) enables reach-in positioning of the spool on the drum, and spool ready release, for disposal.

A motor control on the box, is indicated at 38, for ease of motor control and operation. The motor may typically be a gear motor providing step-down of output RPM, to a low speed level, for slowly winding the spool, for slow line-winding and progressive traction exertion and holding. A line tension sensor 50 is shown in FIG. 3, and its output at 51 may be fed to the motor as for example to stop further tension exertion after a selected tension level is reached. The sensor may be adjustable to increase or decrease the selected or described level of tension exertion.

FIG. 2 shows the provision for position adjustment of the support means for the drum and spool. Such support means may include a support plate 60 carried by the box 13 to be shifted sidewardly (see arrows 61), and clamped in selected sideward position, in accordance with a patient's shifted leg position. Such shifting moves line 20 and traction device 17 to the left or right, a desired amount, for comfort. Plate 60 has an edge portion 60a slidable in a groove 60b in box wall 14; and a clamping screw is provided at 62 to hold plate 60 in selected transverse position.

FIG. 1 shows provision of at least one, and preferably two auxiliary motors as at 75 and 76, controllable as by manually operable controls 75a and 76a, for driving auxiliary drums 77 and 78, the latter having associated lifting lines 77a and 78a extending to different portions of a leg support frame 79, as for example to the front and rear of that frame. Motors 75 and 76, and associated driven spools or drums may be carried by units 86 and 87 carried by an upper horizontal frame 80, and shiftable along that frame 80 to extend over the supported portion of the leg frame 79. The operator can then operate controls 75a and 76a on units 86 and 87 to control winding or unwinding of lines 77a and 78a connected to forward and rearward portions of the frame 79, to precisely tilt, or elevate and/or lower different portions of frame 79 to precisely position the patient's leg under traction; and kit box 13 (from which traction is exerted) can be correspondingly elevated or lowered on bar 11, to control the angle or position of line 20, whereby the direction of traction can be controlled for any elevated positioning of the user's leg. Side to side selected positioning of the traction drum add a further adjusted parameter to such traction control, for maximum effectiveness, and patient comfort. FIGS. 5-9 show alternative forms of the apparatus. FIG. 9 shows laterally shifted position of plate 60. Controls 75a and 76a can be carried at a side or sides of kit box 13', shown in FIG. 6.

A digitized read-out is shown at 99.

Advantages of the device are as follows:

Can be affixed to any type of post or rail in seconds

Full programmability—any physician ordered directives can be fulfilled in seconds with the push of a key pad Securely stores information, dates, and specific patient data which can be printed out with a secure code access Low battery and replace battery warning system Full digital readout LED backlit for easy, safe viewing in dark environments Completely washable with standard disinfectants Works with both skin and skeletal traction applications and disaster environment capable Consumable aspect: replaceable cartridge/module per patient to ensure an aseptic cross contamination free application by way of a "snap in", single use disposable drum A vertically telescoping "spine" or car which allows the unit to be raised upward if necessary for clearance of rope An adjustable base/floor to accommodate a spine board application Spool housing is adjustable from side to side, and rotatable 90°.

Figure 5:
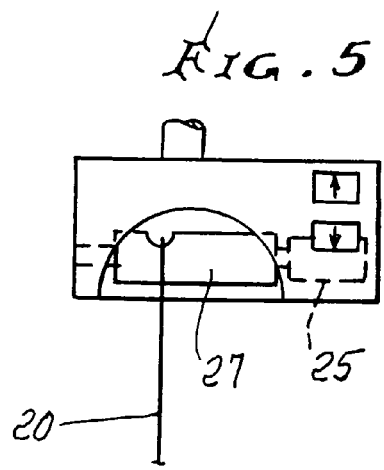
Figure 6:
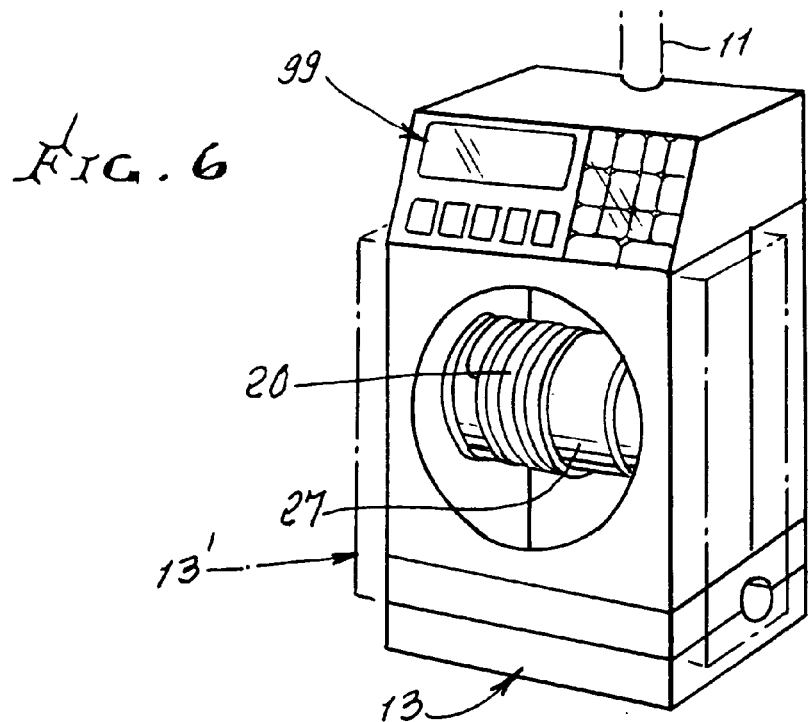
Figure 7:
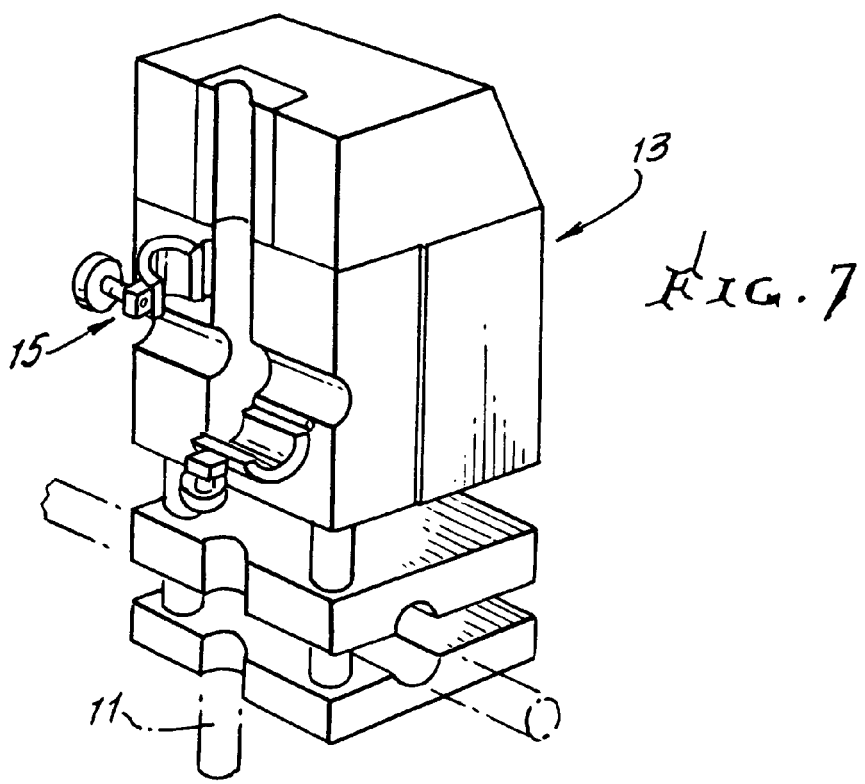
Figure 11:
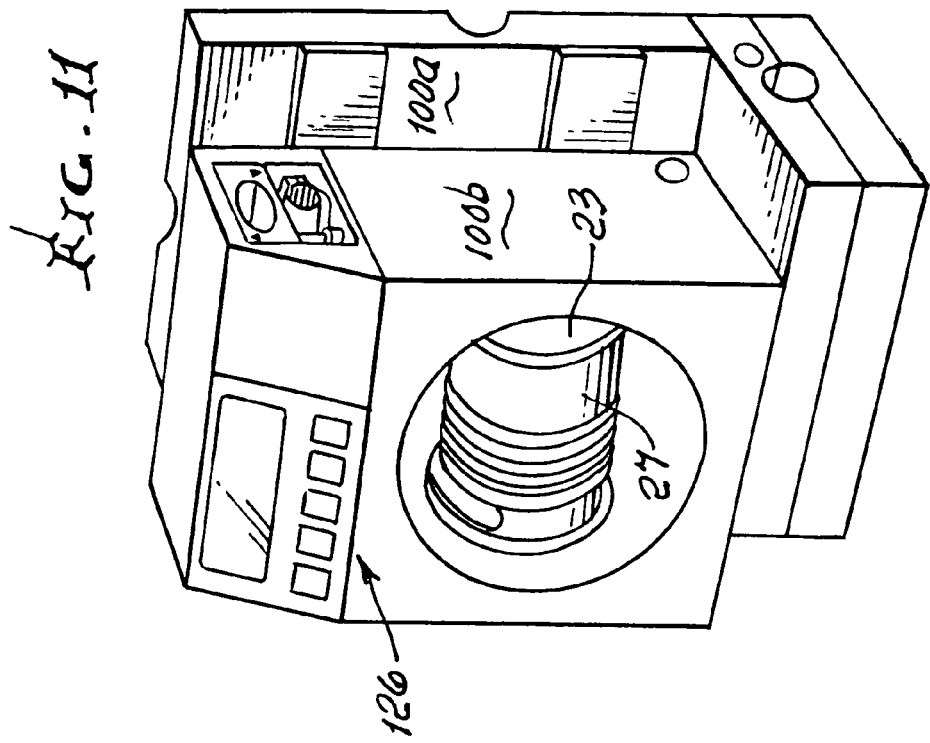
FIGS. 10-13 show satellite drives associated with a kit box, for controlling elevation of a patient's body and/or legs.
Figure 10:
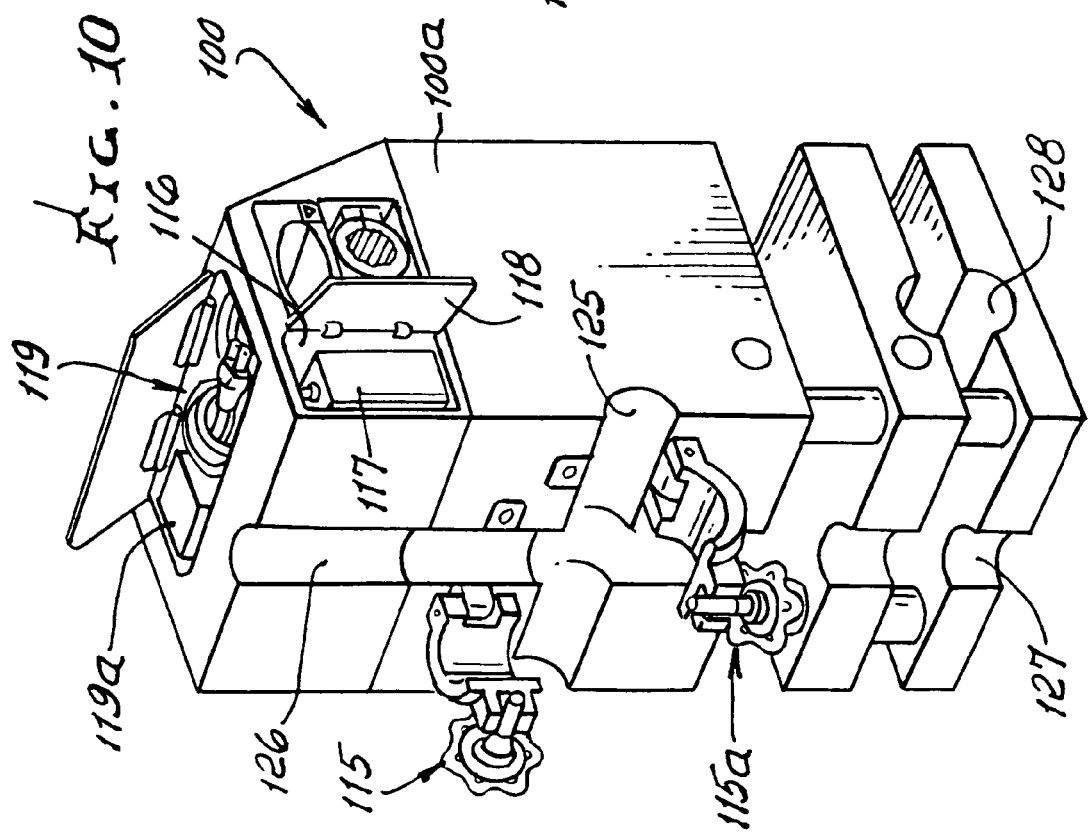

Referring to FIGS. 10 and 11, they show a kit 100 including box 100a, corresponding to box 10 in FIG. 5. It is attachable to fixed bars, as at 11 and 11a at the foot end of a hospital bed, as via holders or clamp 115 and 115a. Recesses 125-128 in the box walls receive the bars, which firmly orient the box.

At the box top is a chamber 116 to receive an electrical battery 117, when door 118 is opened. A top chamber 119 receives a transformer 119a to reduce standard hospital AC voltage to a lower DC voltage, such as 12 VDC, for supply to motor 120 in satellite boxes 121 and 122, corresponding to boxes 75 and 76 seen in FIG. 1, and attachable to horizontal hospital frame bar 80, seen in FIG. 1, as via clamps 121a and 122a. Flexible lines 77a and 78a are wound on disposable drums or reels 77a' and 78a' received into and mounted for rotation in the satellite boxes. Lines 77a and 78a are extended and used to support the frame 79, and the motors have associated controls that are manually controllable.

Figure 12:
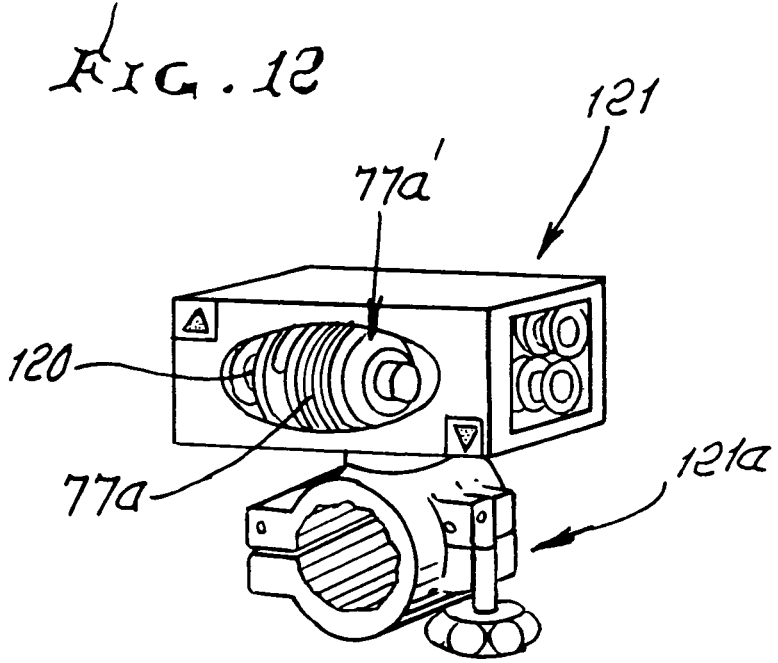
Figure 13:
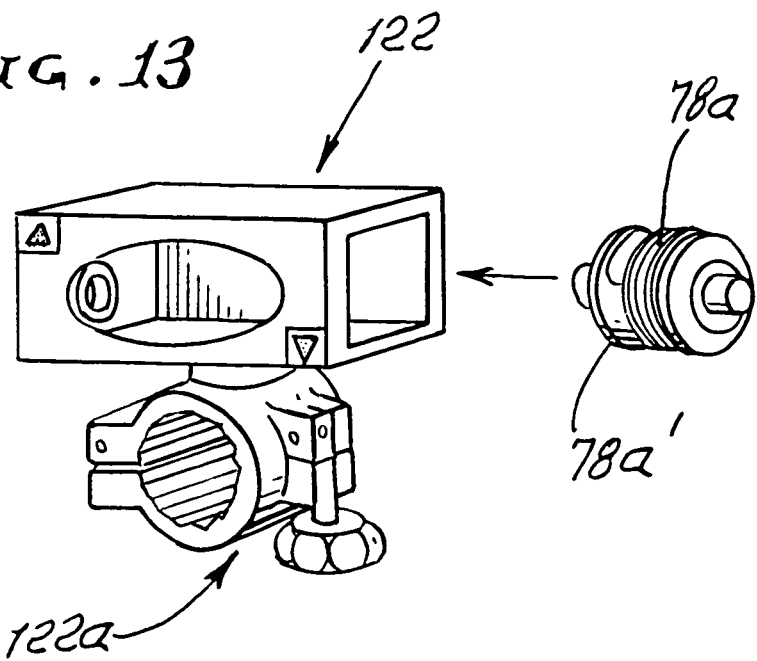

FIG. 11 shows box 100a having two sections 100 band 100c, section 100b being laterally shiftable relative to section 100a, to accommodate to patient shifting position. Line winding disposable spool 27 is releasably attached to drum 23, as referred to above. Controls are carried at 126 on section 100b. See also FIGS. 12 and 13.

What is claimed is:

1. Patient body part traction exerting and control kit apparatus, comprising in combination
   a) a motor driven rotary drive means to tension a traction exerting line,
   b) a support means carrying said rotary drive means and configured to be attached to equipment at a traction exertion site, to present said drive means for traction line operation attached to said rotary drive means,
   c) said support means having a first section attached to said equipment, and a second section carrying said rotary drive means for displacement enabling sideward shifting of said traction line to accommodate patient body shifting, while under traction.

2. The combination of claim 1 wherein said support means has connections enabling selective attachment to said equipment.

3. The combination of claim 2 wherein said support means comprises a housing containing said rotary drive means in a position to receive attachment of a disposable drum to wind said line.

4. The combination of claim 3 including said disposable drum, presented toward an open side of said housing that passes said line at the time of traction line connection to the patient's body part, for traction exertion.

5. The combination of claim 3 including a controllable electric motor carried by said housing and operatively connected to said rotary drive means for controlling rotation thereof, there being motor controls carried by said housing.

6. The combination of claim 3 including a supply of said disposable drums, for selective assembly to said rotary drive means at times of traction exertion application to successive patients' body parts.

7. The combination of claim 1 wherein said second section has linear displacement connection to said first section.

8. The combination of claim 7 wherein the rotary drive means is presented for longitudinal traction line connection, said linear connection allowing transverse displacement of said rotary drive means.

9. The combination of claim 1 including at least one auxiliary motorized control associated with said apparatus for controlling an auxiliary line that extends to a frame positioned to support said body part under traction.

10. The combination of claim 9 wherein said auxiliary control is removably carried by support means.

11. The combination of claim 1 including two motorized auxiliary controls for respectively controlling two auxiliary liens that extend to a frame positioned to support said body part under traction.

12. The combination of claim 11 including said auxiliary lines extending to two different portions of said frame, to control elevation thereof.

13. The combination of claim 3 and including at least one auxiliary motorized control associated with said apparatus for controlling an auxiliary line that extends to a frame positioned to support said body part under traction, said motorized control is removably carried by said container, for removal and manually operable, remotely from the container.

14. The combination of claim 12 wherein there are two of said auxiliary motorized controls, and which are removably carried by said container, for relative removal and manually operable remotely from the container, to control elevation of the frame that supports said body part under traction.

15. Injured patient traction apparatus, comprising in combination:
 a) a carrier,
 b) a roller supported by the carrier,
 c) a tension exerting strand having a first portion rolled on the roller, and a second portion projecting away from the roller,
 d) means to connect the strand second portion to a patient's body part for exerting tension on that part,
 e) the carrier having adjusted position relative to said means, and the roller rollably adjusted to adjust traction force exertion via the strand second portion,
 f) and wherein the carrier has box configuration, and the roller is rotatably mounted in the carrier.

16. The combination of claim 15 including a motor connected to the roller to forcibly adjust its rotated position, thereby to adjust strand tension, the motor carried by the carrier in the form of a box having an open front to pass said strand.

17. The combination of claim 15 including control means for controlling the motor, thereby to control strand tension.

18. The combination of claim 17 including a sensor operatively connected to the roller to sense the amount of strand tension exerted on the patient's body part.

19. The combination of claim 15 includes means to elevate and lower the box and roller therein, relative to the patient support.

20. The combination of claim 15 including a connector connected to the strand sensor portion to releasably connect the strand sensor portion to the patient's body part.

21. The combination of claim 20 wherein the connector has two arms attachable to said body part, and a loop attached to the strand sensor portion.

22. The combination of claim 15 wherein one portion of the carrier is shiftably relative to another mounting portion of the carrier, to shift the roller position, for patient comfort.

\* \* \* \* \*